(12) United States Patent
Ostroff

(10) Patent No.: US 8,543,205 B2
(45) Date of Patent: Sep. 24, 2013

(54) TEMPERATURE SENSOR FOR A LEADLESS CARDIAC PACEMAKER

(75) Inventor: Alan Ostroff, Pleasanton, CA (US)

(73) Assignee: Nanostim, Inc., Sunnyvale, CA (US)

( * ) Notice: Subject to any disclaimer, the term of this patent is extended or adjusted under 35 U.S.C. 154(b) by 0 days.

(21) Appl. No.: 13/272,092

(22) Filed: Oct. 12, 2011

(65) Prior Publication Data
US 2012/0089198 A1    Apr. 12, 2012

Related U.S. Application Data

(60) Provisional application No. 61/392,382, filed on Oct. 12, 2010.

(51) Int. Cl.
*A61N 1/372* (2006.01)
(52) U.S. Cl.
USPC .................................. 607/21; 607/9; 607/17
(58) Field of Classification Search
USPC ............. 607/4, 6, 21, 35, 9, 36, 17; 600/509
See application file for complete search history.

(56) References Cited

U.S. PATENT DOCUMENTS

| | | |
|---|---|---|
| 3,199,508 A | 8/1965 | Roth |
| 3,212,496 A | 10/1965 | Preston |
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |

(Continued)

FOREIGN PATENT DOCUMENTS

| | | |
|---|---|---|
| EP | 1741465 A1 | 1/2007 |
| JP | 05-245215 | 9/1993 |

(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. 7,630,767).

(Continued)

*Primary Examiner* — Joseph Stoklosa
(74) *Attorney, Agent, or Firm* — Shay Glenn LLP

(57) ABSTRACT

A leadless cardiac pacemaker comprises a housing, a plurality of electrodes coupled to an outer surface of the housing, and a pulse delivery system hermetically contained within the housing and electrically coupled to the electrode plurality, the pulse delivery system configured for sourcing energy internal to the housing, generating and delivering electrical pulses to the electrode plurality. The pacemaker further comprises a temperature sensor hermetically contained within the housing and adapted to sense temperature information, wherein the pacemaker can control electrical pulse delivery at least partly based on the temperature information.

10 Claims, 14 Drawing Sheets

(56) References Cited

U.S. PATENT DOCUMENTS

| | | |
|---|---|---|
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A * | 2/1991 | Cook et al. ..................... 607/21 |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A * | 8/1994 | Weijand ..................... 607/21 |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Glele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |

| Patent | Kind | Date | Inventor |
|---|---|---|---|
| 5,571,143 | A | 11/1996 | Hoegnelid et al. |
| 5,571,148 | A | 11/1996 | Loeb et al. |
| 5,579,775 | A | 12/1996 | Dempsey et al. |
| 5,586,556 | A | 12/1996 | Spivey et al. |
| 5,591,217 | A | 1/1997 | Barreras |
| 5,598,848 | A | 2/1997 | Swanson et al. |
| 5,649,952 | A | 7/1997 | Lam |
| 5,650,759 | A | 7/1997 | Hittman et al. |
| 5,654,984 | A | 8/1997 | Hershbarger et al. |
| 5,662,689 | A | 9/1997 | Elsberry et al. |
| 5,669,391 | A | 9/1997 | Williams |
| 5,674,259 | A | 10/1997 | Gray |
| 5,676,153 | A | 10/1997 | Smith et al. |
| 5,693,076 | A | 12/1997 | Kaemmerer |
| 5,694,940 | A | 12/1997 | Unger et al. |
| 5,694,952 | A | 12/1997 | Lidman et al. |
| 5,697,958 | A | 12/1997 | Paul et al. |
| 5,702,427 | A | 12/1997 | Ecker et al. |
| 5,725,559 | A | 3/1998 | Alt et al. |
| 5,728,154 | A | 3/1998 | Crossett et al. |
| 5,730,143 | A | 3/1998 | Schwarzberg |
| 5,735,880 | A | 4/1998 | Prutchi et al. |
| 5,738,102 | A | 4/1998 | Lemelson |
| 5,740,811 | A | 4/1998 | Hedberg et al. |
| 5,741,314 | A | 4/1998 | Daly et al. |
| 5,766,231 | A | 6/1998 | Erickson et al. |
| 5,792,205 | A | 8/1998 | Alt et al. |
| 5,810,735 | A | 9/1998 | Halperin et al. |
| 5,814,076 | A | 9/1998 | Brownlee |
| 5,814,087 | A | 9/1998 | Renirie |
| 5,814,089 | A | 9/1998 | Stokes et al. |
| 5,824,016 | A | 10/1998 | Ekwall |
| 5,871,451 | A | 2/1999 | Unger et al. |
| 5,876,353 | A | 3/1999 | Riff |
| 5,876,425 | A | 3/1999 | Gord et al. |
| 5,891,178 | A | 4/1999 | Mann et al. |
| 5,899,928 | A | 5/1999 | Sholder et al. |
| 5,935,079 | A | 8/1999 | Swanson et al. |
| 5,954,761 | A | 9/1999 | Machek et al. |
| 5,957,861 | A | 9/1999 | Combs et al. |
| 5,984,861 | A | 11/1999 | Crowley |
| 5,987,352 | A | 11/1999 | Klein et al. |
| 5,995,876 | A | 11/1999 | Kruse et al. |
| 5,999,857 | A | 12/1999 | Weijand et al. |
| 6,002,969 | A | 12/1999 | Machek et al. |
| 6,004,269 | A | 12/1999 | Crowley et al. |
| 6,061,596 | A | 5/2000 | Richmond et al. |
| 6,076,016 | A | 6/2000 | Feierbach |
| 6,080,187 | A | 6/2000 | Alt et al. |
| 6,093,146 | A | 7/2000 | Filangeri |
| 6,096,065 | A | 8/2000 | Crowley |
| 6,102,874 | A | 8/2000 | Stone et al. |
| 6,112,116 | A | 8/2000 | Fischell et al. |
| 6,115,628 | A | 9/2000 | Stadler et al. |
| 6,115,630 | A | 9/2000 | Stadler et al. |
| 6,115,636 | A | 9/2000 | Ryan |
| 6,119,031 | A | 9/2000 | Crowley |
| 6,125,290 | A | 9/2000 | Miesel |
| 6,125,291 | A | 9/2000 | Miesel et al. |
| 6,128,526 | A | 10/2000 | Stadler et al. |
| 6,129,751 | A | 10/2000 | Lucchesi et al. |
| 6,132,390 | A | 10/2000 | Cookston et al. |
| 6,132,456 | A | 10/2000 | Sommer et al. |
| 6,134,459 | A | 10/2000 | Roberts et al. |
| 6,134,470 | A | 10/2000 | Hartlaub |
| 6,139,510 | A | 10/2000 | Palermo |
| 6,141,584 | A | 10/2000 | Rockwell et al. |
| 6,141,588 | A | 10/2000 | Cox et al. |
| 6,141,592 | A | 10/2000 | Pauly |
| 6,144,866 | A | 11/2000 | Miesel et al. |
| 6,148,230 | A | 11/2000 | KenKnight |
| 6,152,882 | A | 11/2000 | Prutchi |
| 6,163,723 | A | 12/2000 | Roberts et al. |
| 6,164,284 | A | 12/2000 | Schulman et al. |
| 6,167,310 | A | 12/2000 | Grevious |
| 6,178,349 | B1 | 1/2001 | Kieval |
| 6,178,356 | B1 | 1/2001 | Chastain et al. |
| 6,185,443 | B1 | 2/2001 | Crowley |
| 6,185,452 | B1 | 2/2001 | Schulman et al. |
| 6,185,464 | B1 | 2/2001 | Bonner et al. |
| 6,188,932 | B1 | 2/2001 | Lindegren |
| 6,190,324 | B1 | 2/2001 | Kieval et al. |
| 6,198,952 | B1 | 3/2001 | Miesel |
| 6,201,993 | B1 | 3/2001 | Kruse et al. |
| 6,208,894 | B1 | 3/2001 | Schulman et al. |
| 6,208,900 | B1 | 3/2001 | Ecker et al. |
| 6,223,081 | B1 | 4/2001 | Kerver |
| 6,230,059 | B1 | 5/2001 | Duffin |
| 6,236,882 | B1 | 5/2001 | Lee et al. |
| 6,240,321 | B1 | 5/2001 | Janke et al. |
| 6,243,608 | B1 | 6/2001 | Pauly et al. |
| 6,248,080 | B1 | 6/2001 | Miesel et al. |
| 6,263,245 | B1 | 7/2001 | Snell |
| 6,265,100 | B1 | 7/2001 | Saaski et al. |
| 6,266,554 | B1 | 7/2001 | Hsu et al. |
| 6,266,564 | B1 | 7/2001 | Hill et al. |
| 6,272,379 | B1 | 8/2001 | Fischell et al. |
| 6,280,409 | B1 | 8/2001 | Stone et al. |
| 6,289,229 | B1 | 9/2001 | Crowley |
| 6,306,088 | B1 | 10/2001 | Krausman et al. |
| 6,310,960 | B1 | 10/2001 | Saaski et al. |
| 6,315,721 | B2 | 11/2001 | Schulman et al. |
| 6,324,418 | B1 | 11/2001 | Crowley et al. |
| 6,324,421 | B1 | 11/2001 | Stadler et al. |
| RE37,463 | E | 12/2001 | Altman |
| 6,343,227 | B1 | 1/2002 | Crowley |
| 6,343,233 | B1 | 1/2002 | Werner et al. |
| 6,347,245 | B1 | 2/2002 | Lee et al. |
| 6,358,202 | B1 | 3/2002 | Arent |
| 6,361,522 | B1 | 3/2002 | Scheiner et al. |
| 6,363,282 | B1 | 3/2002 | Nichols et al. |
| 6,364,831 | B1 | 4/2002 | Crowley |
| 6,370,434 | B1 | 4/2002 | Zhang et al. |
| 6,381,492 | B1 | 4/2002 | Rockwell et al. |
| 6,381,493 | B1 | 4/2002 | Stadler et al. |
| 6,381,494 | B1 | 4/2002 | Gilkerson et al. |
| 6,383,209 | B1 | 5/2002 | Crowley |
| 6,385,593 | B2 | 5/2002 | Linberg |
| 6,386,882 | B1 | 5/2002 | Linberg |
| 6,397,100 | B2 | 5/2002 | Stadler et al. |
| 6,402,689 | B1 | 6/2002 | Scarantino et al. |
| 6,405,073 | B1 | 6/2002 | Crowley et al. |
| 6,405,083 | B1 | 6/2002 | Rockwell et al. |
| 6,409,674 | B1 | 6/2002 | Brockway et al. |
| 6,409,675 | B1 | 6/2002 | Turcott |
| 6,412,490 | B1 | 7/2002 | Lee |
| 6,418,346 | B1 | 7/2002 | Nelson et al. |
| 6,423,056 | B1 | 7/2002 | Ishikawa et al. |
| 6,424,866 | B2 | 7/2002 | Mika et al. |
| 6,428,484 | B1 | 8/2002 | Battmer et al. |
| 6,434,429 | B1 | 8/2002 | Kraus et al. |
| 6,438,410 | B2 | 8/2002 | Hsu et al. |
| 6,438,417 | B1 | 8/2002 | Rockwell et al. |
| 6,442,433 | B1 | 8/2002 | Linberg |
| 6,444,970 | B1 | 9/2002 | Barbato |
| 6,445,953 | B1 | 9/2002 | Bulkes et al. |
| 6,458,145 | B1 | 10/2002 | Ravenscroft et al. |
| 6,459,928 | B2 | 10/2002 | Mika et al. |
| 6,459,937 | B1 | 10/2002 | Morgan et al. |
| 6,466,820 | B1 | 10/2002 | Juran et al. |
| 6,468,263 | B1 | 10/2002 | Fischell et al. |
| 6,470,215 | B1 | 10/2002 | Kraus et al. |
| 6,471,645 | B1 | 10/2002 | Warkentin et al. |
| 6,472,991 | B1 | 10/2002 | Schulman et al. |
| 6,477,424 | B1 | 11/2002 | Thompson et al. |
| 6,480,733 | B1 | 11/2002 | Turcott |
| 6,482,154 | B1 | 11/2002 | Haubrich et al. |
| 6,484,055 | B1 | 11/2002 | Marcovecchio |
| 6,484,057 | B2 | 11/2002 | Ideker et al. |
| 6,490,487 | B1 | 12/2002 | Kraus et al. |
| 6,496,715 | B1 | 12/2002 | Lee et al. |
| 6,498,951 | B1 | 12/2002 | Larson et al. |
| 6,500,168 | B1 | 12/2002 | Jellie |
| 6,501,983 | B1 | 12/2002 | Natarajan et al. |
| 6,512,949 | B1 | 1/2003 | Combs et al. |
| 6,512,959 | B1 | 1/2003 | Gomperz et al. |
| 6,522,926 | B1 | 2/2003 | Kieval et al. |
| 6,522,928 | B2 | 2/2003 | Whitehurst et al. |

| Patent No. | Date | Name |
|---|---|---|
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0141995 A1 | 7/2003 | Lin |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0043765 A1 | 2/2005 | Williams et al. |
| 2005/0075682 A1* | 4/2005 | Schulman et al. .............. 607/48 |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |

| | | | |
|---|---|---|---|
| 2006/0121475 A1 | 6/2006 | Davids et al. | |
| 2006/0135999 A1 | 6/2006 | Bodner et al. | |
| 2006/0136004 A1 | 6/2006 | Cowan et al. | |
| 2006/0161222 A1 | 7/2006 | Haubrich et al. | |
| 2006/0241705 A1 | 10/2006 | Neumann et al. | |
| 2006/0247750 A1 | 11/2006 | Seifert et al. | |
| 2006/0282150 A1 | 12/2006 | Olson et al. | |
| 2007/0016263 A1 | 1/2007 | Armstrong et al. | |
| 2007/0043414 A1 | 2/2007 | Fifer et al. | |
| 2007/0088394 A1 | 4/2007 | Jacobson | |
| 2007/0088396 A1 | 4/2007 | Jacobson | |
| 2007/0088397 A1 | 4/2007 | Jacobson | |
| 2007/0088398 A1 | 4/2007 | Jacobson | |
| 2007/0088400 A1* | 4/2007 | Jacobson | 607/21 |
| 2007/0123923 A1 | 5/2007 | Lindstrom et al. | |
| 2007/0142709 A1 | 6/2007 | Martone et al. | |
| 2007/0179552 A1 | 8/2007 | Dennis et al. | |
| 2007/0270675 A1* | 11/2007 | Kane et al. | 600/315 |
| 2007/0276004 A1 | 11/2007 | Hirsch et al. | |
| 2007/0276444 A1 | 11/2007 | Gelbart et al. | |
| 2007/0293904 A1 | 12/2007 | Gelbart et al. | |
| 2008/0004535 A1 | 1/2008 | Smits | |
| 2008/0021532 A1 | 1/2008 | Kveen et al. | |
| 2008/0039738 A1 | 2/2008 | Dinsmoor et al. | |
| 2008/0086168 A1 | 4/2008 | Cahill | |
| 2008/0091255 A1 | 4/2008 | Caparso et al. | |
| 2008/0119911 A1 | 5/2008 | Rosero | |
| 2008/0243218 A1 | 10/2008 | Bottomley et al. | |
| 2008/0269591 A1 | 10/2008 | Halperin et al. | |
| 2009/0082827 A1 | 3/2009 | Kveen et al. | |
| 2009/0082828 A1 | 3/2009 | Ostroff | |
| 2009/0149902 A1 | 6/2009 | Kumar et al. | |
| 2009/0171408 A1 | 7/2009 | Solem | |
| 2010/0069983 A1 | 3/2010 | Peacock et al. | |
| 2010/0198288 A1 | 8/2010 | Ostroff | |
| 2010/0249828 A1 | 9/2010 | Mavani et al. | |
| 2010/0292541 A1 | 11/2010 | Hashiba et al. | |
| 2010/0305653 A1 | 12/2010 | Lund et al. | |
| 2010/0305656 A1 | 12/2010 | Imran et al. | |
| 2010/0312332 A1 | 12/2010 | Forster et al. | |
| 2011/0004117 A1* | 1/2011 | Neville et al. | 600/546 |
| 2011/0071586 A1 | 3/2011 | Jacobson | |
| 2011/0077708 A1 | 3/2011 | Ostroff | |
| 2011/0208260 A1 | 8/2011 | Jacobson | |
| 2011/0218587 A1 | 9/2011 | Jacobson | |
| 2011/0282423 A1 | 11/2011 | Jacobson | |

FOREIGN PATENT DOCUMENTS

| | | |
|---|---|---|
| JP | 06/507096 | 3/2006 |
| JP | 06/516449 | 7/2006 |
| WO | WO93/12714 A1 | 7/1993 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |
| WO | WO 2008/058265 A2 | 5/2008 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

Bordacher et al.; Impact and prevention of far-field sensing in fallback mode switches; PACE; vol. 26 (pt. II); pp. 206-209; Jan. 2003.

Brandt et al.; Far-field QRS complex sensing: prevalence and timing with bipolar atrial leads; PACE; vol. 23; pp. 315-320; Mar. 2000.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; Feb. 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; Feb. 2005.

Lüchinger ; Safety aspects of cardiac pacemakers in magnetic resonance imaging; Dissertation submitted to the Swiss Federal Institute of Technology Zurich; 137 pages; 2002 (month unavailable).

Nyenhuis et al.; MRI and Implanted Medical Devices: Basic Interactions with an emphasis on heating; vol. 5; No. 3; pp. 467-480; Sep. 2005.

Shellock et al.; Cardiac pacemaker: in vitro assessment at 1.5 T; Am Heart J; vol. 151; No. 2; pp. 436-43; Feb. 2006.

Khairkhahan et al.; U.S. Appl. No. 13/272,074 entitled "Delivery catheter systems and methods," filed Oct. 12, 2011.

Khairkhahan et al.; U.S. Appl. No. 13/272,082 entitled "Leadless cardiac pacemaker with anti-unscrewing feature," filed Oct. 12, 2011.

Khairkhahan et al.; U.S. Appl. No. 13/324,781 entitled "Delivery Catheter Systems and Methods," filed Dec. 13, 2011.

Jacobson et al.; U.S. Appl. No. 13/277,151 entitled "Leadless cardiac pacemaker with conducted communication," filed Oct. 19, 2011.

Khairkhahan et al.; U.S. Appl. No. 13/324,802 entitled "Pacemaker Retrieval Systems and Methods ," filed Dec. 13, 2011.

Khairkhahan et al.; U.S. Appl. No. 13/331,922 entitled "Leadless Pacemaker with Radial Fixation Mechanism ," filed Dec. 20, 2011.

* cited by examiner

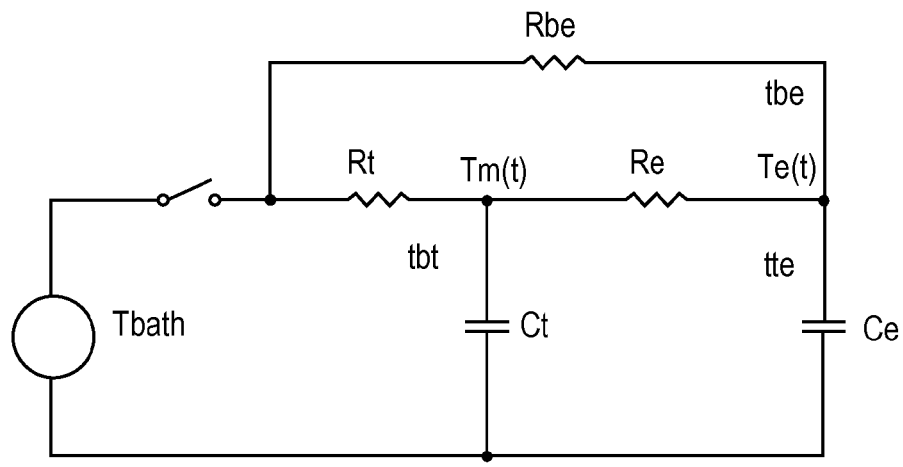

Let:

t = time since immersion in bath
    Th = bath temperature
    Tc = start temperature
    Tm(t) = thermistor temperature, measured
    Tt(t) = thermistor temperature, simulated
    Te(t) = adhesive + silicone temperature, simulated
    $\tau bt$ = bath-to-thermistor time constant
    $\tau be$ = bath-to-adhesive + silicone time constant
    $\tau te$ = thermistor-to-adhesive + silicone time constant Then:

$$\frac{Th - Te(t)}{Th - Tc} = e^{\frac{t}{\tau be}}$$

$$Te(t) = Th - (Th - Tc) \cdot e^{\frac{t}{\tau be}}$$

$$Tt(t2) - Tt(t1) = \left[\frac{Th - Tt(t1)}{\tau bt} - \frac{Tt(t1) - Te(t1)}{\tau te}\right] \cdot (t2 - t1)$$

FIG. 6

Time constants derived from Example 1:

| symbol | parameter | value | units |
|---|---|---|---|
| τbt | Bath-to-thermistor time constant | 4.3 | seconds |
| τbe | Bath-to-adhesive + silicone time constant | 9.7 | seconds |
| τte | Thermistor-to-adhesive + silicone time constant | 1.5 | seconds |

Time constants derived from Example 2:

| symbol | parameter | value | units |
|---|---|---|---|
| τbt | Bath-to-thermistor time constant | 3.0 | seconds |
| τbe | Bath-to-adhesive time constant | 10.0 | seconds |
| τte | Thermistor-to-adhesive time constant | 6.0 | seconds |

Time constants derived from Example 3:

| symbol | parameter | value | units |
|---|---|---|---|
| τbt | Bath-to-thermistor time constant | 4.0 | seconds |
| τbe | Bath-to-adhesive time constant | 9.7 | seconds |
| τte | Thermistor-to-adhesive time constant | 1.5 | seconds |

Time constants derived from Example 4:

| symbol | parameter | value | units |
|---|---|---|---|
| $\tau_{bt}$ | Bath-to-thermistor time constant | 3.4 | seconds |
| $\tau_{be}$ | Bath-to-adhesive time constant | 3.4 | seconds |
| $\tau_{te}$ | Thermistor-to-adhesive time constant | ∞ | seconds |

Time constants derived from Example 5:

| symbol | parameter | value | units |
|---|---|---|---|
| $\tau_{bt}$ | Bath-to-thermistor time constant | 5.5 | seconds |
| $\tau_{be}$ | Bath-to-air time constant | 16.0 | seconds |
| $\tau_{te}$ | Thermistor-to-air time constant | 3.9 | seconds |

Time constants derived from Example 6:

| symbol | parameter | value | units |
|---|---|---|---|
| τbt | Bath-to-thermistor time constant | 11.8 | seconds |
| τbe | Bath-to-wire time constant | 23.3 | seconds |
| τte | Thermistor-to-wire time constant | 3.9 | seconds |

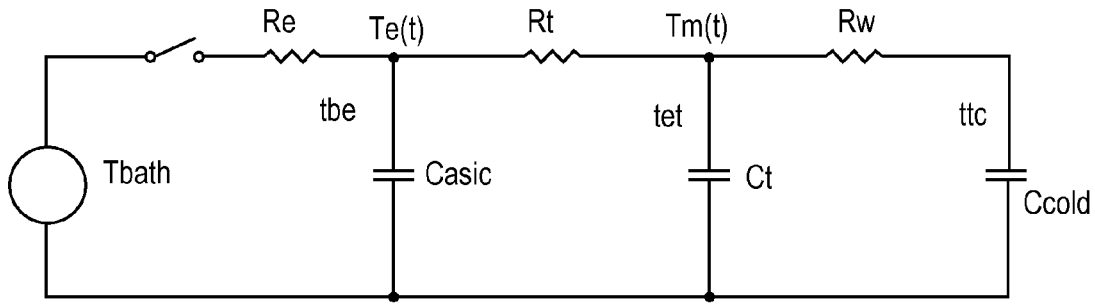

Let:
  t = time since immersion in bath
  Th = bath temperature
  Tc = start temperature
  Tm(t) = thermistor temperature, measured
  Tt(t) = thermistor temperature, simulated
  Te(t) = ASIC-temperature, simulated
  τet = ASIC-to-thermistor time constant
  τbe = bath-to-ASIC time constant
  τtc = thermistor-to-wire time constant Then:

$$\frac{Th - Te(t)}{Th - Tc} = e^{\frac{t}{tbe}}$$

$$Te(t) = Th - (Th - Tc) \cdot e^{\frac{t}{tbe}}$$

$$Tt(t2) - Tt(t1) = \left[\frac{Te(t1) - Tt(t1)}{\tau et} - \frac{(Tt(t1) - Tc)}{\tau tc}\right] \cdot (t2 - t1)$$

FIG. 13

Time constants derived from Example 7:

| symbol | parameter | value | units |
|---|---|---|---|
| τet | ASIC-to-thermistor time constant | 1.4 | seconds |
| τbe | Bath-to-ASIC time constant | 12.9 | seconds |
| τtc | Thermistor-to-wire time constant | 100 | seconds |

TEMPERATURE SENSOR FOR A LEADLESS CARDIAC PACEMAKER

CROSS REFERENCE TO RELATED APPLICATIONS

This application claims the benefit of U.S. Provisional Patent Application No. 61/392,382, filed Oct. 12, 2010, titled "Temperature Sensor for a Leadless Cardiac Pacemaker", which application is incorporated herein by reference in its entirety.

This application incorporates herein by reference in their entirety for all purposes the following patent applications, all by Peter M. Jacobson: U.S. Patent Publication Nos. (1) U.S.2007/0088394A1, (2) U.S.2007/0088396A1, (3) U.S.2007/0088397A1, (4) U.S.2007/0088398A1, (5) U.S.2007/0088400A1, (6) U.S.2007/0088405A1, (7) U.S.2007/0088418A1, and International Publication No. WO/2007/047681A2.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to leadless cardiac pacemakers. More specifically, this disclosure describes the use of temperature sensors in leadless cardiac pacemakers.

BACKGROUND

Cardiac pacing by an artificial pacemaker provides an electrical stimulation of the heart when the heart's own natural pacemaker and/or conduction system fails to provide synchronized atrial and ventricular contractions at rates and intervals sufficient for a patient's health. Such antibradycardial pacing provides relief from symptoms and even life support for hundreds of thousands of patients.

The rate of stimulation provided by a pacemaker may need to be adjusted to match the level of the patient's physical activity. Prior rate responsive pacemakers have relied on, among other parameters, central venous temperature to indicate the need to adjust stimulation rates up or down. Prior devices often used temperature sensors connected to the pacemaker body by a lead extending from the pacemaker body's location outside of the heart to a temperature sensor located within the patient's heart. Two examples of prior rate-responsive pacemakers may be found in U.S. Pat. No. 5,411,535 and U.S. Patent Publication No. 2007/0088400.

SUMMARY OF THE DISCLOSURE

In one embodiment, a leadless cardiac pacemaker is provided comprising a hermetic housing adapted and configured to be disposed in a chamber of a human heart, a battery disposed in the housing, at least two electrodes supported by the housing, a temperature sensor supported by the housing, and a controller disposed in the housing and adapted to sense intracardiac information using the two electrodes and deliver stimulation energy from the battery to the electrodes using temperature information from the temperature sensor.

In some embodiments, the temperature sensor comprises a thermistor. In one embodiment, the thermistor is bonded to an interior surface of the housing. In some embodiments, the thermistor is mounted on a header assembly of the housing.

In one embodiment of the pacemaker, the controller comprises an ASIC and the temperature sensor comprises a semiconductor temperature sensor incorporated into the ASIC.

In one embodiment, the leadless cardiac pacemaker further comprises a bonded thermal path between the temperature sensor and the housing. In one embodiment, the bonded thermal path is a thermal pad.

In some embodiments, the temperature sensor is disposed within the housing. In other embodiments, the temperature sensor is not directly attached to the housing. In yet another embodiment, the temperature sensor is disposed outside of the can.

A method for providing electrical pacing signals to a patient's heart is also provided, comprising sensing intracardiac information via two electrodes in contact with tissue within a chamber of the heart and supported by a hermetic housing disposed within the chamber, providing electrical stimulation signals to the heart at a stimulation rate using the electrodes, sensing temperature with a temperature sensor supported by the housing, and adjusting the stimulation rate of electrical stimulation signals using a controller disposed within the housing based on the temperature.

In some embodiments, the sensing step comprises sensing the temperature with a thermistor. In other embodiments, the sensing step comprises sensing the temperature with a thermistor bonded to an interior surface of the housing. In additional embodiments, the sensing step comprises sensing the temperature with a thermistor mounted on a header assembly of the housing. In yet another embodiment, the sensing step comprises sensing the temperature with a semiconductor temperature sensor incorporated into an ASIC containing the controller. In another embodiment, the sensing step comprises sensing the temperature with a temperature sensor disposed within the housing. In one embodiment, the sensing step comprises sensing the temperature with a temperature sensor disposed outside the housing.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6 is one embodiment of a thermal circuit for use in a leadless cardiac pacemaker.

FIG. 13 is another embodiment of a thermal circuit for use in a leadless cardiac pacemaker.

DETAILED DESCRIPTION OF THE INVENTION

This disclosure relates to a rate responsive leadless cardiac pacemaker or other leadless biostimulator. The leadless biostimulator can be implanted within a chamber of the patient's heart. Instead of measuring central venous temperature using a temperature sensor on a lead extending from the biostimulator housing, embodiments of the rate responsive leadless biostimulator of this disclosure can employ a temperature sensor supported by the biostimulator housing. The leadless biostimulator of this disclosure can use the measured temperature to adjust the rate of its electrical stimulation signals using a controller disposed within the housing.

Some embodiments of a leadless biostimulator may include a hermetic housing disposed in a chamber of a human heart, a battery disposed in the housing, at least two electrodes supported by the housing, a temperature sensor supported by the housing and a controller disposed in the housing. The controller can be adapted to sense intracardiac information using the two electrodes and to deliver stimulation energy from the battery to the electrode using temperature information from the temperature sensor. The temperature sensor may be supported by the leadless biostimulator housing in any manner consistent with the thermal time constant requirements of the system. The temperature sensor may be a thermistor or a semiconductor temperature sensor incorporated into the controller.

In order to use central venous temperature as the metabolic parameter for a rate response algorithm, the leadless biostimulator may be able to sense and respond to changes in central venous temperatures within a clinically significant period of time, such as less than 30 seconds. Since the leadless biostimulator will be disposed in contact with the patient's blood within the patient's heart, the biostimulator design can provide a heat conduction path from the blood to the temperature sensing element whose time constant is sufficiently small to allow the sensor to reach its final value within the chosen clinically significant time. Thus, for example, if the desired clinically significant time is 30 seconds, the thermal time constant of the temperature sensing components might be chosen to be 10 seconds.

Figure 1:
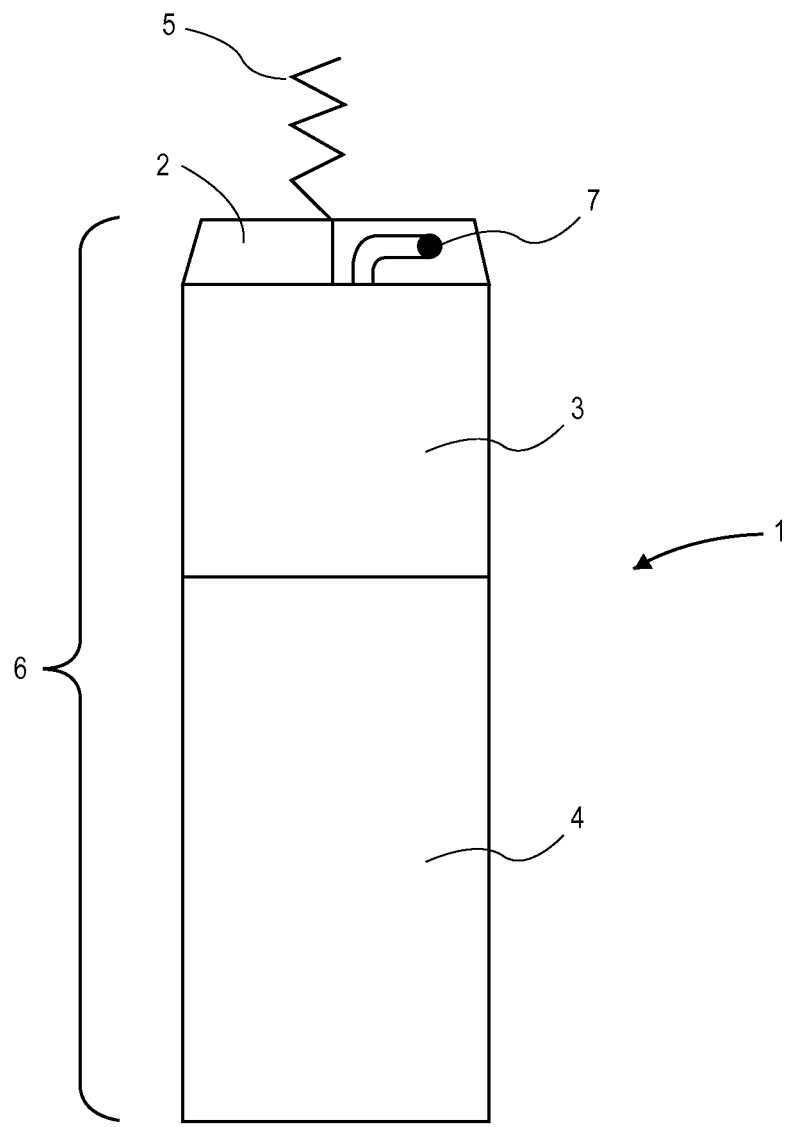
FIG. 1 shows a leadless cardiac pacemaker including a temperature sensor.

FIG. 1 shows a leadless cardiac pacemaker or leadless biostimulator 1. Biostimulator 1 can include a housing 6 having a header section 2 made from an electrically insulating material and extending from a hermetic can 3 and 4 made from, e.g., titanium. Can section 3 can be electrically insulated, and can section 4 may not insulated so that it can serve as an electrode. An electronics compartment within the cans 3 and 4 can contain the electronic components necessary for operation of the biostimulator, including a battery and a controller. A helical fixation device 5 can extend through a passage in can 3 into and through header 2 as shown. In some embodiments, the fixation device 5 can comprise an electrode, and in other embodiments a distal electrode can be separate from the helical fixation device. Other details of leadless biostimulators may be found in the copending applications referenced above and incorporated by reference herein.

In the embodiment of FIG. 1, a thermistor 7 can disposed in header 2. The thermistors can include at least two thermistors leads for electrically connecting the thermistors 7 to the controller of the leadless biostimulator. In this embodiment, at least one of the thermistor leads can extend through a feedthrough in can section 3 to a controller within the can. The other thermistor lead may be electrically connected to the can, or can alternatively pass through a feedthrough into the interior of the can. In this embodiment, thermistor 7 can be in contact with an interior surface of header 2 and thus can be in thermal contact with blood surrounding the biostimulator through header 2. The controller inside housing 6 can be adapted to sense intracardiac information using electrodes 4 and 5 and to deliver stimulation energy from the battery to electrodes on the leadless biostimulator using temperature information from the thermistor 7. In some embodiments, the rate of stimulation provided by a pacemaker may need to be adjusted to match the level of the patient's physical activity or temperature. For example, the temperature information can determine the temperature of the patient and adjust the rate of stimulation to account for temperature variations due to fever or exercise.

Figure 2:
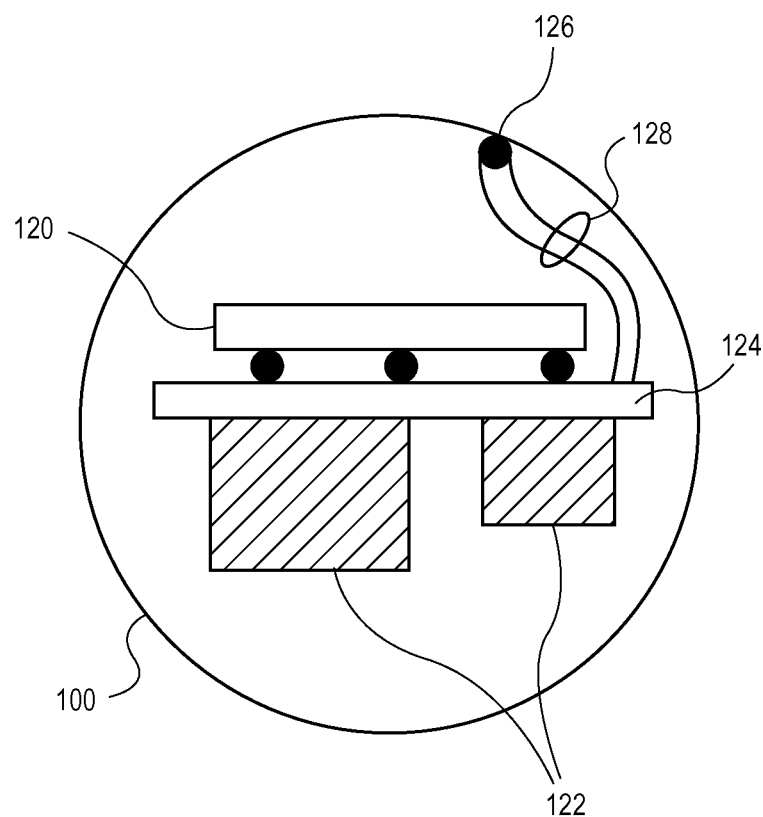
FIG. 2 illustrates a temperature sensor disposed within a hermetic housing of a leadless cardiac pacemaker.

In the embodiment of FIG. 2, the temperature sensor can be a thermistor 126 disposed within a hermetic can 100 of the housing. As shown in this cross-sectional view, thermistor 126 can be bonded so as to be thermally connected to an inside surface of hermetic can 100, and the thermistors can connect to ASIC controller 120 via leads 128 and substrate 124. Thus, thermistor 126 can be configured to sense the temperature of blood surrounding the biostimulator through housing 100. Other elements within hermetic can 100 include the ASIC substrate 124, other electronic components 122, and a battery (not shown). At least two electrodes can be supported by, and exterior to, the housing as in the embodiment of FIG. 1. In some embodiments, the ASIC 120 can be adapted to sense intracardiac information using the electrodes and to deliver stimulation energy from the battery to one of the electrodes using temperature information from the thermistor 126.

Figure 3:
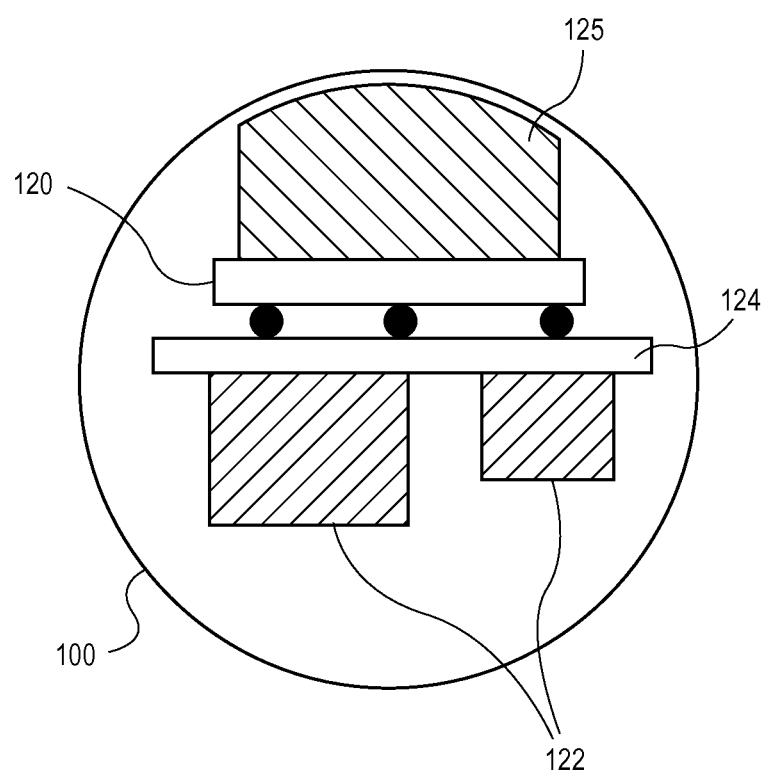
FIG. 3 illustrates a semiconductor temperature sensor integrated into an ASIC in a leadless cardiac pacemaker.

In the embodiment of FIG. 3, the temperature sensor can be a semiconductor temperature sensor integrated into ASIC 124. A thermally conductive pad 125 can extend from the temperature sensor in ASIC 124 to an interior surface of housing 100. Thus, the temperature sensor can sense the temperature of blood surrounding the biostimulator through housing 100 with conductive pad 125. As in the embodiment of FIG. 2, at least two electrodes can be supported by, and exterior to, the housing. The ASIC 120 can be adapted to sense intracardiac information using the electrodes and to deliver stimulation energy from the battery to one of the electrodes using temperature information from the integrated temperature sensor.

Figure 4:
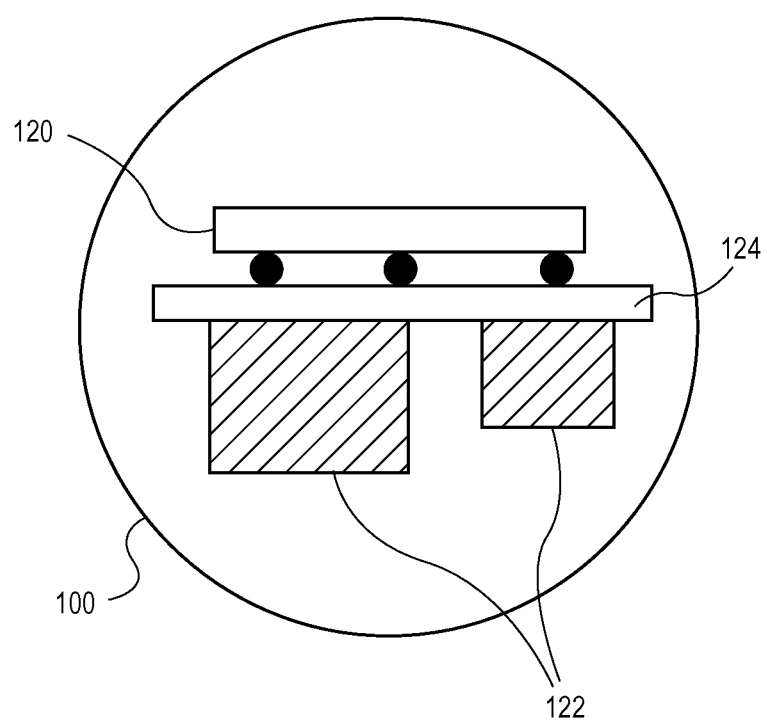
FIG. 4 illustrates another embodiment of a semiconductor temperature sensor integrated into an ASIC in a leadless cardiac pacemaker.

The embodiment of FIG. 4 is similar to that of FIG. 3, but omits the thermally conductive pad. Thus, the temperature sensor integrated into ASIC 120 senses the temperature of blood surrounding the biostimulator via the thermal resistance between the ASIC 120 and the can 100. Similarly, in this embodiment, the ASIC 120 can be adapted to sense intracardiac information using the electrodes and to deliver stimulation energy from the battery to one of the electrodes using temperature information from the integrated temperature sensor.

EXAMPLE 1

Figure 5A:
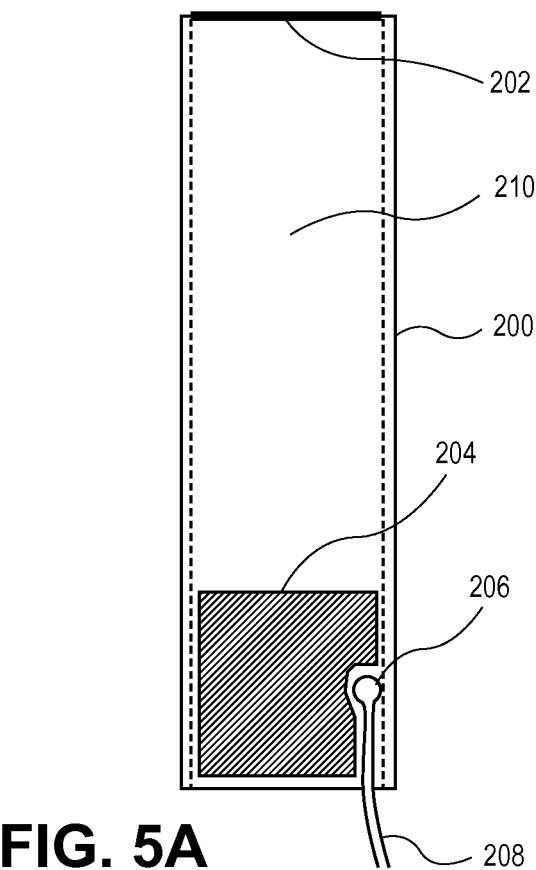
FIGS. 5A and 5B illustrate one embodiment of a leadless cardiac pacemaker with a thermistors temperature sensor.
Figure 5B:
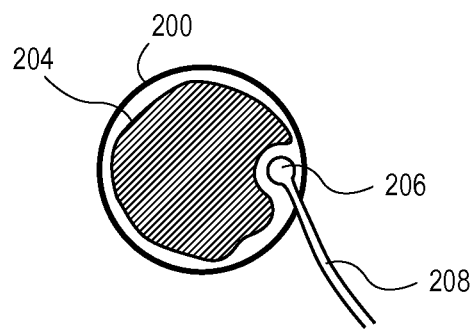

Tests were conducted to see how thermal response times compared among some of these embodiments. FIGS. 5A and 5B show a first prototype assembly having a housing 200 made from a tube capped off at ends 202 and 204 with silicone. The tube can be an 8 mm stainless steel tube, for example. A thermistor 206 was encapsulated with cyanoacrylate to bond it to the inside of housing 200 within the silicone at end 204. Silicone grease was applied between the thermistor and the housing wall contact point. Wires 208 extending from thermistor 206 were insulated. The cavity 210 within housing 200 was filled with water. Housing 200 had a 7 mm diameter and 25.5 mm length. The silicone at end 204 extended 6.5 mm into housing 200.

Two beakers were filled with 500 ml of distilled water and immersed a thermistor in each beaker to monitor temperature. The second beaker was then placed on a hot plate/stirrer and the temperature was adjusted approximately 10° C. higher than the first beaker. The stirrer ran to agitate the solution. The prototype assembly was immersed in the first beaker for at least 5 minutes and transferred the prototype assembly to the second beaker in less than 1 second. The temperature was recorded from all three sensors (one on each beaker and one on the prototype assembly) for a sample rate greater or equal to 1 second/sample for at least 1 minute after transferring the prototype assembly to the second beaker. It was verified that the temperature in the second beaker does not change by more than 5% during the course of the procedure.

Figure 7:
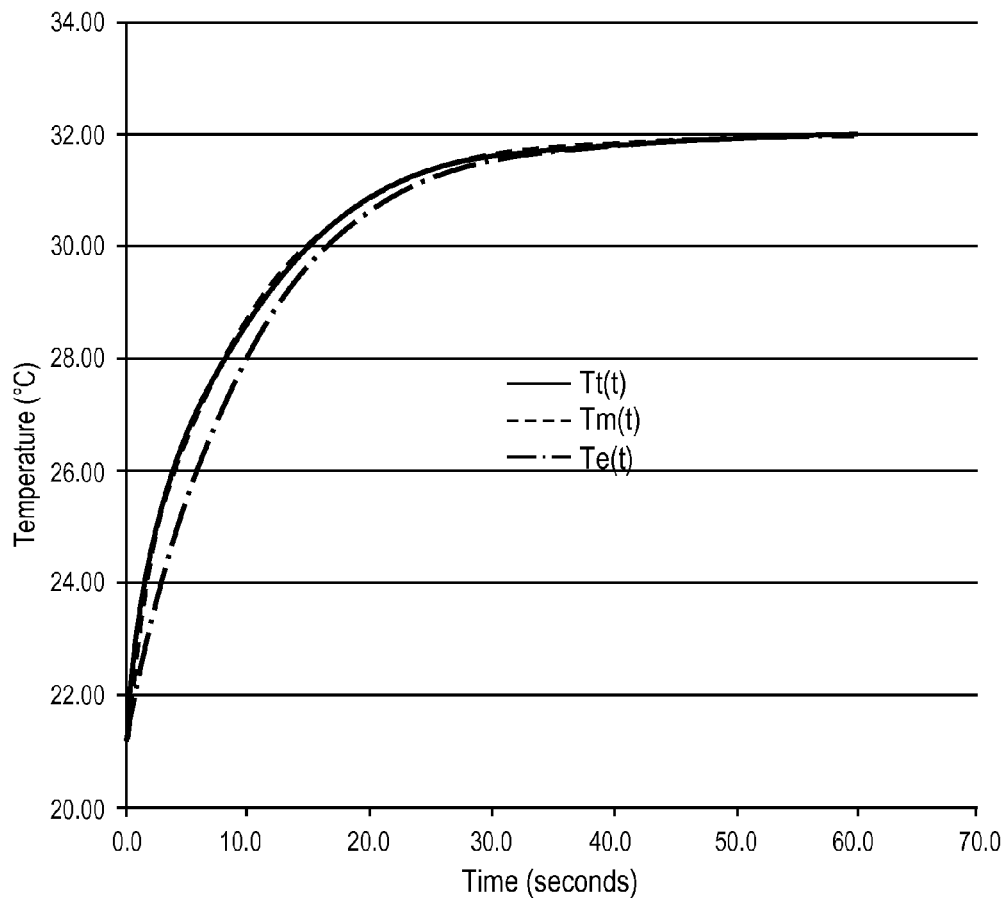
FIG. 7 illustrates a thermal model based on the thermal circuit of FIG. 6.

The measured temperatures were compared with a thermal model based on the thermal circuit shown in FIG. 6. The results are shown in FIG. 7. The model time constants are derived by minimizing the RMS error in Tm(t)−Tt(t) over all time. For each experiment the derived time constants are given. In this case the thermal time constant between the bath and thermistor was determined to be 4.3 seconds.

Let: t=time since immersion in bath; Th=bath temperature; Tc=start temperature; Tm(t)=thermistor temperature, measured; Tt(t)=thermistor temperature, simulated; Te(t)=adhesive+silicone temperature, simulated; τbt=bath-to-thermistor time constant; τbe=bath-to-adhesive+silicone time constant; τte=thermistor-to-adhesive+silicone time constant.

Then:

$$\frac{Th - Te(t)}{Th - Tc} = e^{\frac{-t}{\tau be}}$$

$$Te(t) = Th - (Th - Tc) \cdot e^{-\frac{t}{\tau be}}$$

$$Tt(t2) - Tt(t1) = \left[\frac{Th - Tt(t1)}{\tau bt} - \frac{Tt(t1) - Te(t1)}{\tau te}\right] \cdot (t2 - t1).$$

EXAMPLE 2

Figure 8:
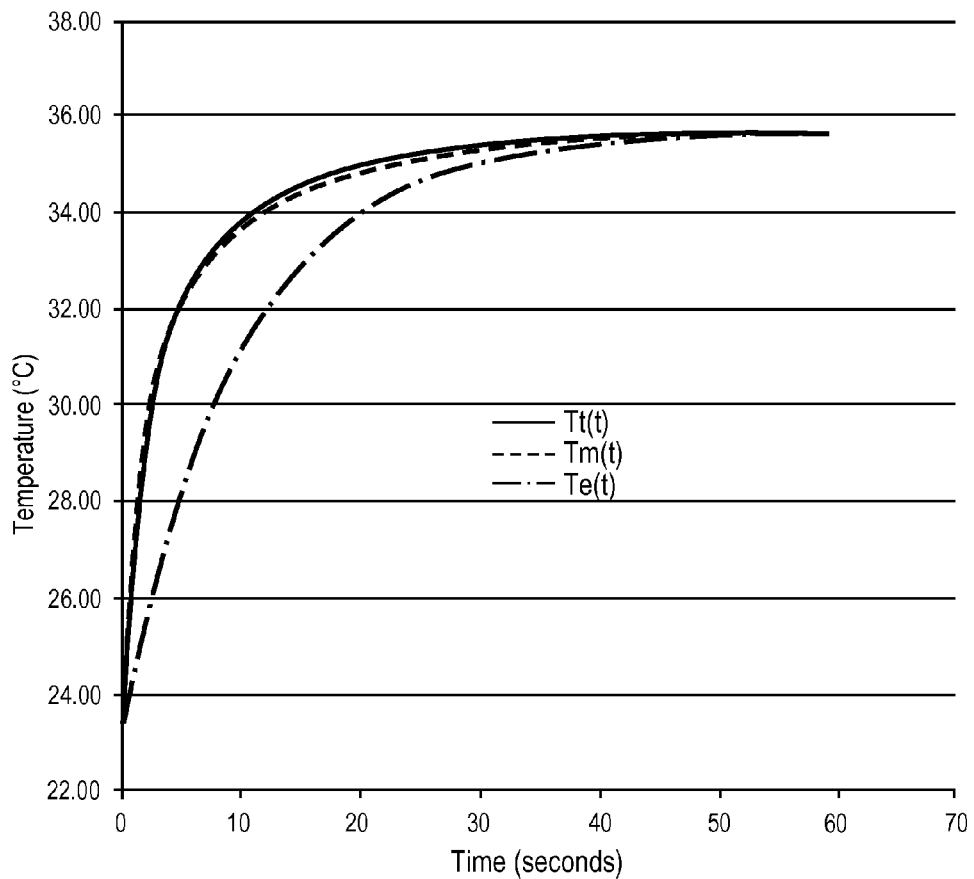
FIG. 8 illustrates a thermal model based on one embodiment of the temperature sensor of FIGS. 5A-5B.

Another test was conducted using a prototype similar to that of FIGS. 5A-5B but using much less cyanoacrylate adhesive to bond the thermistor to the can. The same test protocol was used as in Example 1. The results are shown in FIG. 8. The thermal time constant between the bath and thermistor was determined to be 3.0 seconds.

EXAMPLE 3

Figure 9:
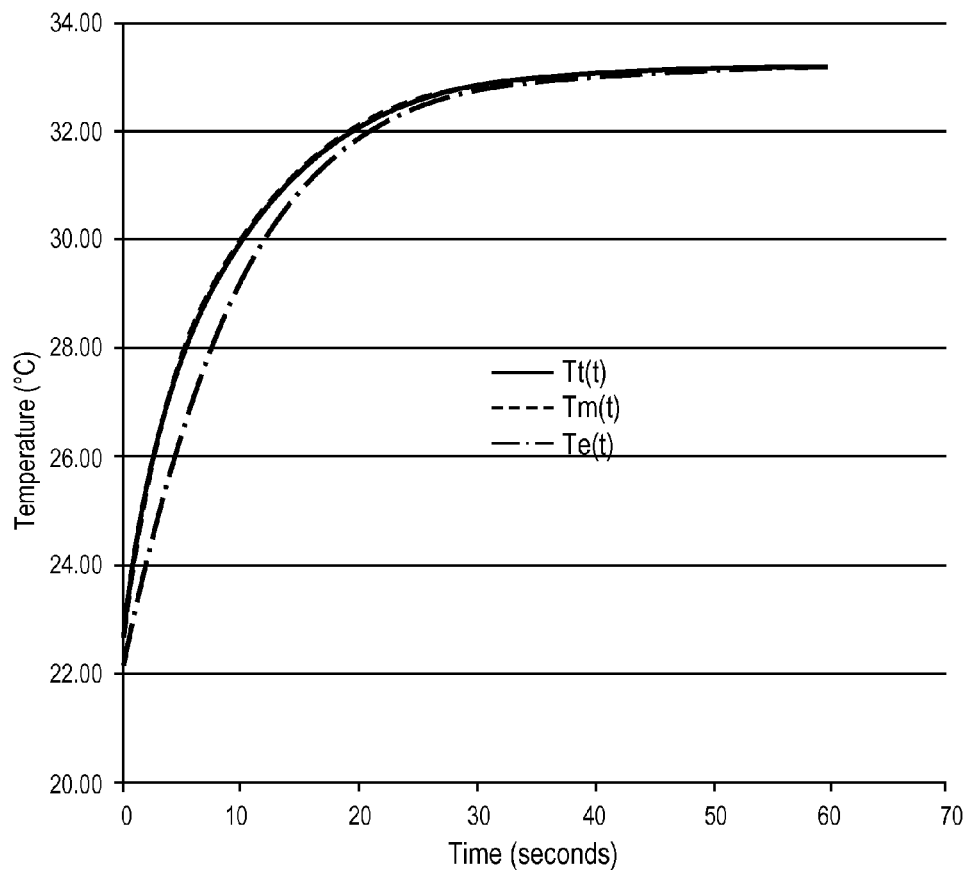
FIG. 9 illustrates a thermal model based on another embodiment of the temperature sensor of FIGS. 5A-5B.

A test was conducted using the test protocol of Example 1 with a prototype similar to that of FIGS. 5A-5B but filled with air instead of water. The results are shown in FIG. 9. The thermal time constant between the bath and thermistor was determined to be 4.0 seconds and therefore the thermal mass of the battery is not expected to greatly change these results.

EXAMPLE 4

Figure 10:
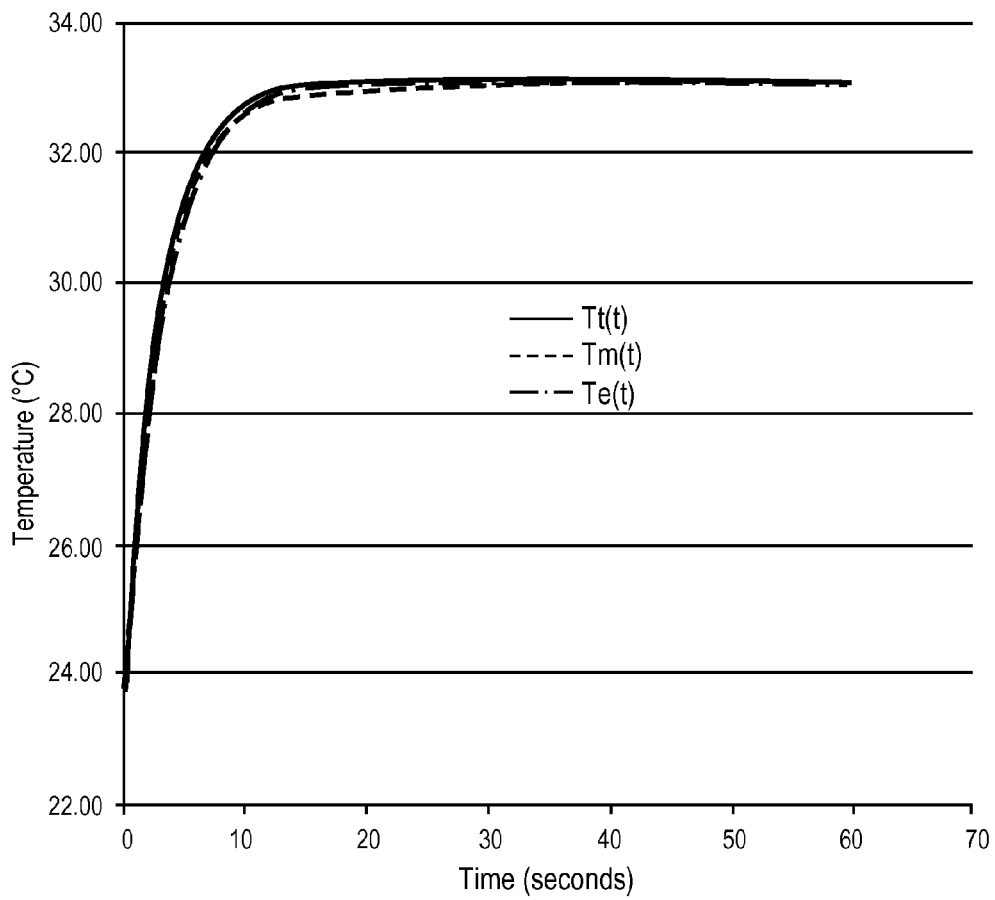
FIG. 10 illustrates a thermal model based on yet another embodiment the temperature sensor of FIGS. 5A-5B.

A test was conducted using the test protocol of Example 1 with a prototype similar to that of FIGS. 5A-5B but with an air gap between the silicone plug and the adhesive/thermistor, and using only a very small amount of cyanoacrylate adhesive to bond the thermistor to the can. The results are shown in FIG. 10. The thermal time constant between the bath and thermistor was determined to be 3.4 seconds.

EXAMPLE 5

Figure 11:
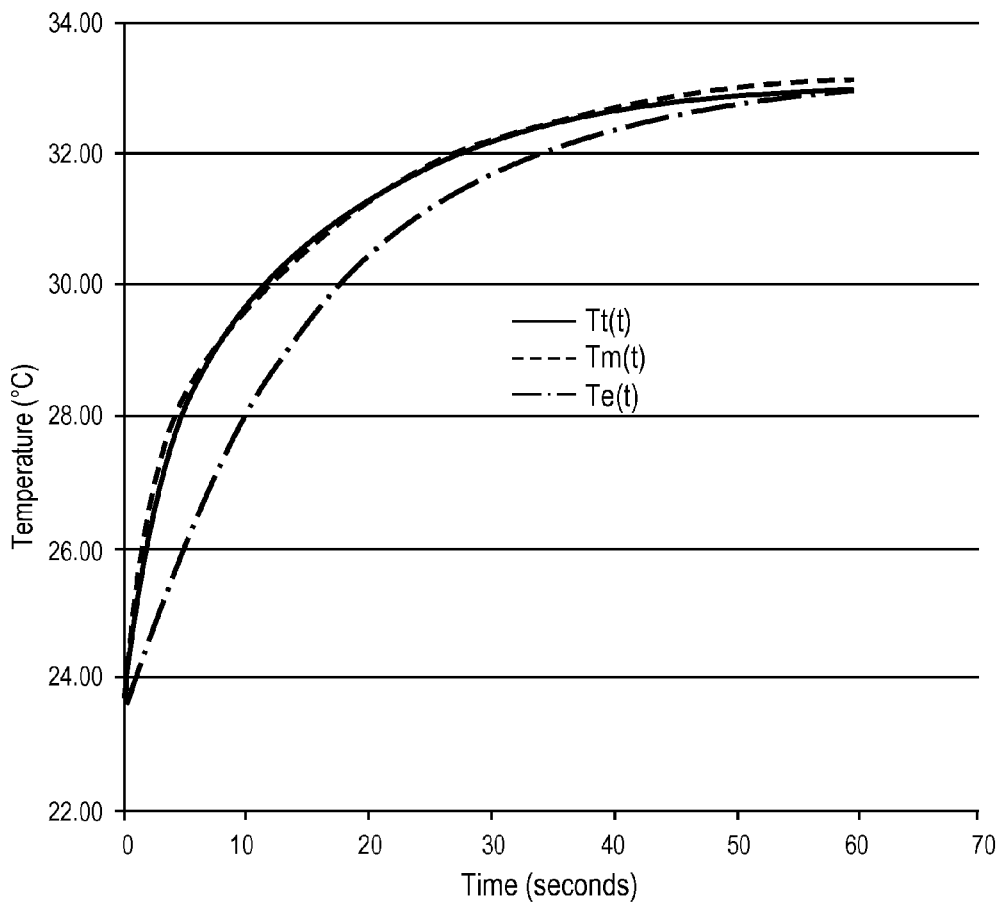
FIG. 11 illustrates a thermal model based on one embodiment of the temperature sensor of FIGS. 5A-5B.

A test was conducted using the test protocol of Example 1 with a prototype similar to that of FIGS. 5A-5B but with the thermistor floating in, not bonded to, the can and with the can filled with air instead of water. The results are shown in FIG. 11. The thermal time constant between the bath and thermistor was also determined to be 5.5 seconds.

EXAMPLE 6

Figure 12:
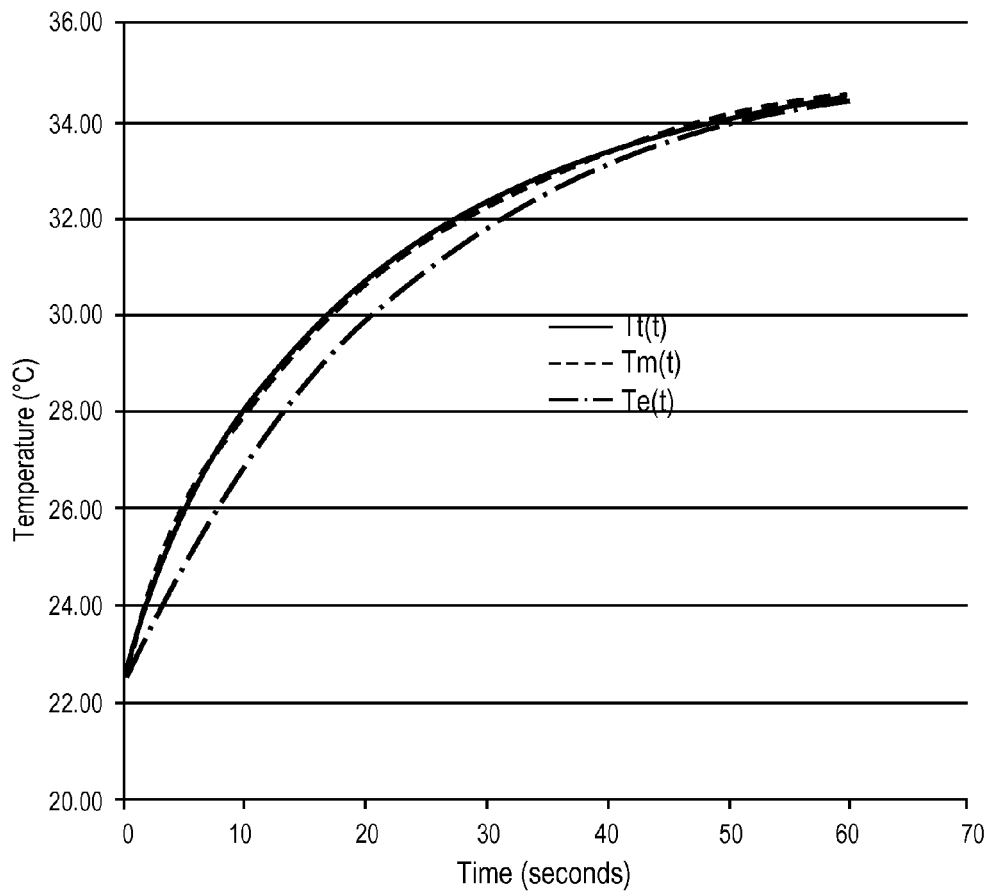
FIG. 12 illustrates a thermal model based on another embodiment of the temperature sensor of FIGS. 5A-5B.

A test was conducted using the test protocol of Example 1 with a prototype similar to that of FIGS. 5A-5B but with the thermistor floating in the can, with the insulated wires leading from the thermistor contained within a straw to further insulate the wires from the bath temperature, and with the can filled with air instead of water. The results are shown in FIG. 12. The thermal time constant between the bath and thermistor was determined to be 11.8 seconds.

EXAMPLE 7

Figure 14:
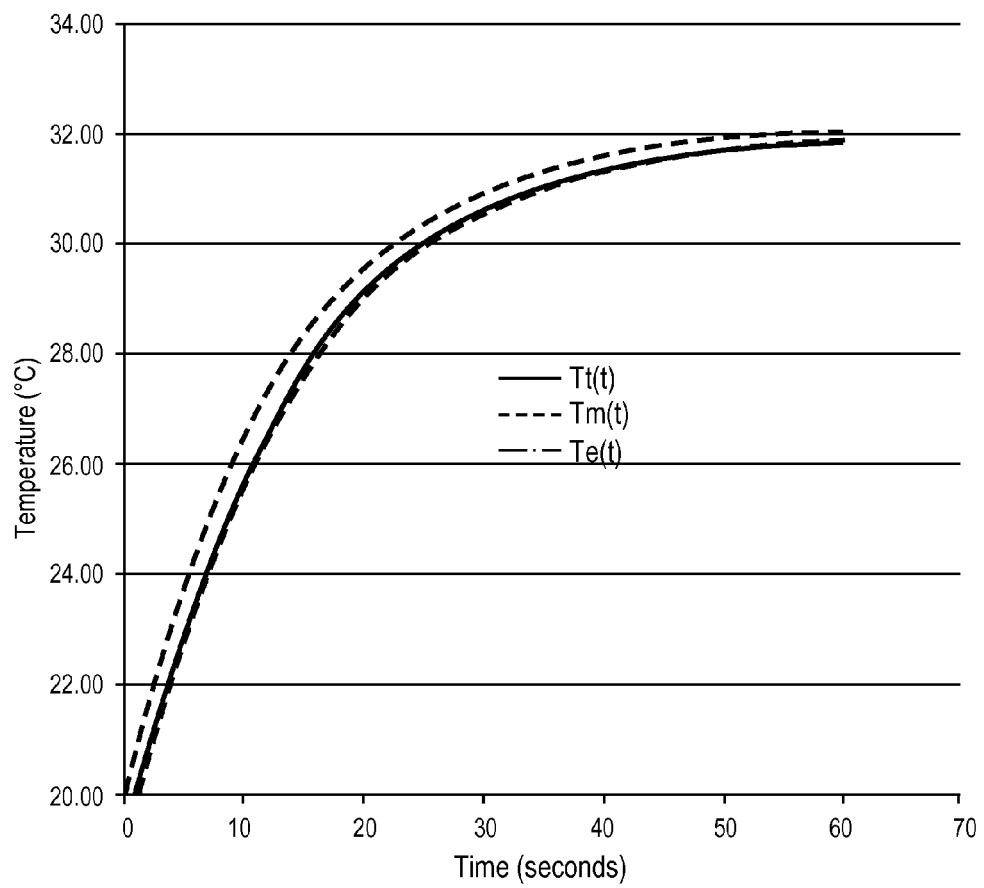
FIG. 14 illustrates a thermal model based on the thermal circuit of FIG. 13.

A test was conducted using the test protocol of Example 1 with a prototype similar to that of FIGS. 5A-5B but with the thermistor bonded to a semiconductor chip within the can. The chip dimensions were 4 mm×5 mm×20 mils. The semiconductor/thermistor assembly was wrapped in one layer of polyimide tape, and the thermistor wires were thermally insulated from the bath using a straw. The can was filled with air, not with water. In this simulation, the model was altered to allow the semiconductor chip (simulating an ASIC) to gain heat from the bath at a first time constant, the thermistor to gain heat from the ASIC at a second time constant, and the thermistor to lose heat to the wires at a third time constant. The thermal model is shown in FIG. 13. The results of this test are shown in FIG. 14. The bath to ASIC time constant was determined to be 12.9 seconds. This test suggests that the thermal time constant between an integrated AISC thermal sensor with no specific thermal connection between the can and ASIC provides acceptable thermal results within the housing of a leadless cardiac pacemaker.

In some embodiments, the temperature sensor may be a thermistor, a semiconductor temperature sensor, or part of an ASIC containing the controller. The sensed temperature is used by the leadless stimulator control circuitry to adjust a rate of electrical stimulation provided by the biostimulator to the patient's heart.

The temperature sensor may sense temperate in a range between 36° C. to 42° C. The low end of the temperature range allows for normal body temperature (37° C.), less circadian variations and less a dip in temperature due to exercise. The high end of the temperature range allows for normal body temperature, plus fever, plus the increase in temperature due to exercise. The resolution may be about 0.023° C. This represents better than $1/5^{th}$ of the smallest anticipated dip amplitude during exercise (0.15° C.).

Unless defined otherwise, all technical terms used herein have the same meanings as commonly understood by one of ordinary skill in the art of cardiac technologies. Specific methods, devices, and materials may be described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs that have been referred to by trade names, brand names, or common names, that these terms or names are provided as contemporary examples, and the invention is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of the invention, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A leadless cardiac pacemaker comprising:
   a hermetic housing adapted and configured to be disposed in a chamber of a human heart;
   a battery disposed in the housing;
   at least two electrodes supported by the housing;
   a temperature sensor disposed in the housing but not bonded to the housing; and
   a controller disposed in the housing and adapted to sense intracardiac information using the two electrodes and deliver stimulation energy from the battery to the electrodes using temperature information from the temperature sensor.

2. The leadless cardiac pacemaker of claim 1 wherein the temperature sensor comprises a thermistor.

3. The leadless cardiac pacemaker of claim 2 wherein the thermistor is mounted on a header assembly of the housing.

4. The leadless cardiac pacemaker of claim 1 wherein the controller comprises an ASIC and the temperature sensor comprises a semiconductor temperature sensor incorporated into the ASIC.

5. The method of claim 1 wherein the temperature sensor is not thermally bonded to the housing.

6. A method for providing electrical pacing signals to a patient's heart comprising:
   sensing intracardiac information via two electrodes in contact with tissue within a chamber of the heart and supported by a hermetic housing disposed within the chamber;
   providing electrical stimulation signals to the heart at a stimulation rate using the electrodes;
   sensing temperature with a temperature sensor disposed in the housing but not bonded to the housing; and
   adjusting the stimulation rate of electrical stimulation signals using a controller disposed within the housing based on the temperature.

7. The method of claim 6 wherein the sensing step comprises sensing the temperature with a thermistor.

8. The method of claim 7 wherein the sensing step comprises sensing the temperature with a thermistor mounted on a header assembly of the housing.

9. The method of claim 6 wherein the sensing step comprises sensing the temperature with a semiconductor temperature sensor incorporated into an ASIC containing the controller.

10. The method of claim 6 wherein the temperature sensor is not thermally bonded to the housing.

* * * * *